United States Patent [19]

Pryor et al.

[11] Patent Number: 5,062,829

[45] Date of Patent: Nov. 5, 1991

[54] RELATES TO DEVICES FOR ADMINISTERING A SUBSTANCE SUCH AS A DRUG OR CHEMICAL OR THE LIKE

[75] Inventors: Raymond J. Pryor; James F. Pharoah; Graham F. Duirs, all of Hamilton, New Zealand

[73] Assignee: Carter Holt Harvey Plastic Products Group Limited, Hamilton, New Zealand

[21] Appl. No.: 495,029

[22] Filed: Mar. 16, 1990

[30] Foreign Application Priority Data

Mar. 17, 1989 [NZ] New Zealand .................. 228382

[51] Int. Cl.[5] ........................................... A61M 31/00
[52] U.S. Cl. ......................... 604/57; 424/438; 604/890.1; 604/891.1; 604/892.1
[58] Field of Search ............... 128/738; 424/425, 438, 424/468; 604/14, 15, 19, 28, 31, 50, 54, 285, 288, 890.1, 891.1, 892.1, 57

[56] References Cited

U.S. PATENT DOCUMENTS

| | | |
|---|---|---|
| 3,811,423 | 5/1974 | Dickinson, III et al. |
| 4,308,859 | 1/1982 | Child ................................. 604/54 |
| 4,687,480 | 8/1987 | Laby et al. ...................... 424/438 |
| 5,002,772 | 3/1991 | Curatolo et al. .................. 424/438 |

FOREIGN PATENT DOCUMENTS

| | | | |
|---|---|---|---|
| 0449029 | 3/1972 | Australia ............................. 424/438 |
| 0942667 | 2/1974 | Canada ................................ 424/425 |
| 0010987 | 5/1980 | European Pat. Off. ............ 424/438 |
| 0164927 | 12/1985 | European Pat. Off. ............ 424/438 |
| 2077103 | 12/1981 | United Kingdom ............... 424/438 |
| 8600519 | 1/1986 | United Kingdom ............... 604/890 |

Primary Examiner—Stephen C. Pellegrino
Assistant Examiner—Glenn K. Dawson
Attorney, Agent, or Firm—Fleit, Jacobson, Cohn, Price, Holman & Stern

[57] ABSTRACT

The device for insertion into a body cavity e.g. the rumen of an animal for example a cattle beast is in the form of a resilient helical coil with bio-degradable portions. The device is deformable to have a smaller dimension to enable insertion through a body passage into the animal cavity. The device carries a drug e.g. progesterone and is retained in the body cavity for a time during which the drug is active. After time has passed the device is broken up by bio-degrading activity into pieces small enough to be discharged naturally by the animal. An applicator is provided.

16 Claims, 2 Drawing Sheets

RELATES TO DEVICES FOR ADMINISTERING A SUBSTANCE SUCH AS A DRUG OR CHEMICAL OR THE LIKE

This invention relates to devices for administering a substance such as a drug or chemical or the like into a live animal and is intended particularly though not solely for administering drugs through the digestive system of ruminant animals such as cattle.

It is an object of the invention to provide a device for administering a substance such as a drug or chemical or the like into a live animal which will at least provide the public with a useful choice.

Accordingly, in one aspect, the invention consists in a device for insertion into a body cavity of an animal, when in one configuration and to lie against walls of said body cavity in an expanded configuration, said device comprising a plurality of interconnected elements, and connectors between said elements, said connectors and/or said elements being constructed of a bio-degradable material.

In a further aspect, the invention consists in a device for insertion into a body cavity of an animal to release a desired substance therein over time, said device being in the form of a helical coil at least parts of which are resilient, said helical coil at least partly including a desired substance in a form adapted to be released from said device over time, said helical coil being resiliently extendible into a first configuration having dimensions small enough so that said helical coil is able to be passed through body passages of said animal into the desired body cavity, and being resiliently biased towards a second configuration having at least one relatively greater dimension over said first configuration whereby the device is in use retained within said body cavity.

In a still further aspect the invention consists in a combination of a device according to either of the two preceding paragraphs and an applicator comprising a chamber so dimensioned and configured as to retain said device in a configuration of reduced width and a plunger portion to eject said coil from said chamber.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

Figure 1:
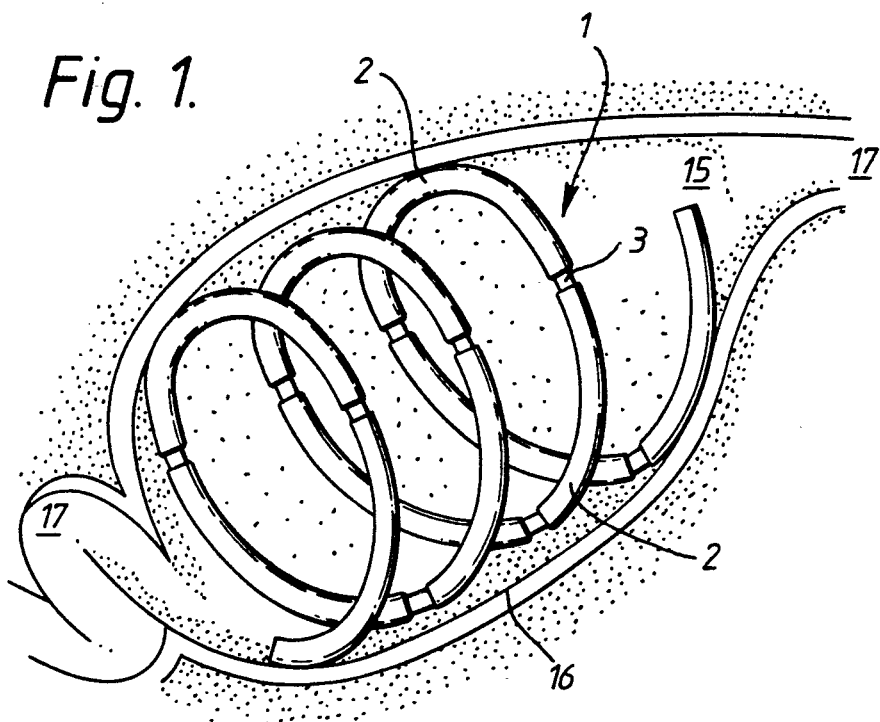
FIG. 1 shows a device in accordance with the invention when placed in the body cavity of an animal.

Referring to the drawings according to the invention, a device is provided for insertion into a body cavity such as the rumen of a ruminant animal such as a cattle beast to release a desired substance such as a drug therein over time. The device in the preferred form, is in the form of a helical coil 1 comprising a plurality of primary elements in the form of segments 2 joined together by one or more secondary elements in the form of connectors 3 the connectors 3 and/or the segments 2 being constructed of a bio-degradable material e.g. a biodegradable polymer such as which will degrade and disintegrate after being subjected to animal body fluids for a period of time.

Figure 2:
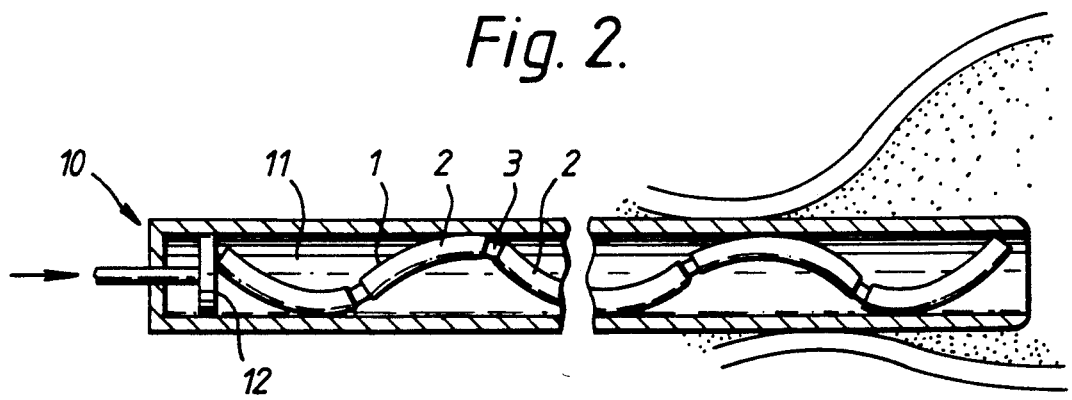
FIG. 2 shows a device in accordance with the invention combined with an applicator positioned for insertion of the device into an animal.

The helical coil 1 is resiliently extendible e.g. by lengthwise extension into a first configuration, shown in FIG. 2, having dimensions, in particular width, allowing it to be passed into an animal through body passages connecting with the desired body cavity. Thus, for example, if the device is to be utilised for example in a ruminant animal such as a cattle beast for example by being passed through the oesophagus into the rumen of the animal, then the device should be of suitable dimensions when extended into the first configuration to pass through the oesophagus. A diameter when extended of about 40 mm has been found to be suitable in this application to cattle beasts.

The coil is resiliently biased towards a second configuration, shown in FIG. 1, which has at least one relatively larger dimension i.e. width or diameter compared with the first dimension shown in FIG. 2. The diameter of the coil illustrated, when in the second configuration, is such as to cause the device to be retained within the desired body cavity of an animal, for example within the rumen of a cattle beast, by expanding and pressing against at least a considerable area of the wall of the body cavity, and by being of too great a diameter to pass through the passages leading into or out of the body cavity.

The segments 2 may in a preferred form comprise moulded material 6 moulded about a spine 7. The segments may have the desired substance and a carrier therefor impregnated in or forming a matrix of a moulded material but the carrier may be coated with the desired substance.

However a spine or a central core 7 is preferably provided which may also include the substance to be administered. For example the moulded portion 6 may comprise a matrix of a silicone elastomer material as the carrier impregnated with a desired drug e.g. progesterone. The spine 7 is preferably constructed of a polyamide e.g. nylon or the like plastics material.

More than one matrix layer may be provided over all or part of each spine, the layers being of the same or different potency of desired substance with outer layers leaching away to expose inner layers and some of the layers need not necessarily contain a drug but may be provided as an inert material to leach away to expose a drug containing layer for release at a later time.

Figure 3:
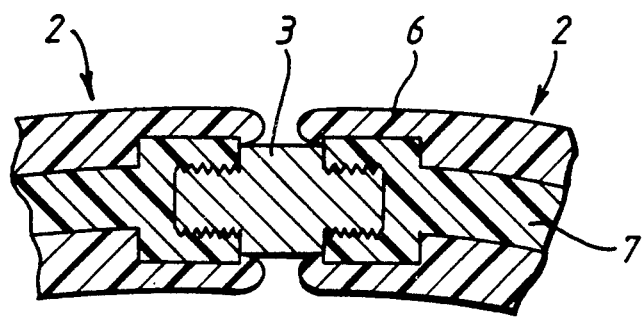
FIG. 3 shows a detail of a connector forming part of a device in accordance with the invention.
Figure 4:
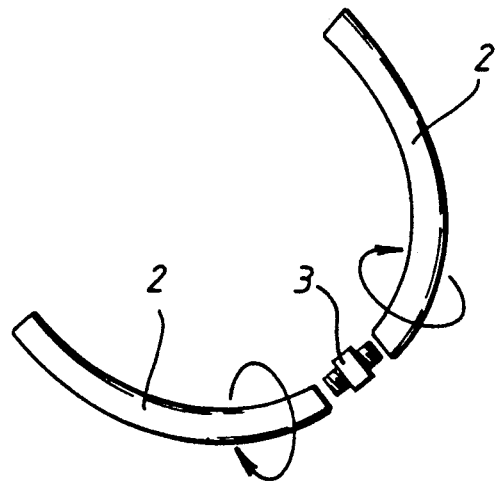
FIG. 4 shows diagramatically the connection mechanism forming part of a device in accordance with the invention and FIG. 5 is a diagram of an alternative form of the invention.

The connectors 3 are constructed of a bio-degradable material which is selected so as to be degraded within the animal, such as by body fluids within the body cavity, and thus allow release of the segments from connection with one another, preferably after substantially all of the administered substance has been released from the device although degradation of the connectors may make a central core substance available for leaching as is explained herein later. The connectors 3 at least in the preferred form of the invention are screw or snap on fastened to the spine portions of the segments, as shown in FIG. 3 or may be integrally moulded with the segments or parts thereof. FIG. 4 shows one possible method of fastening together two segments using a connector, the segments 2 being rotated as indicated by the curved arrows in order to fasten the female threaded spines 7 (shown in FIG. 3) to the male threaded connector 3.

Figure 5:
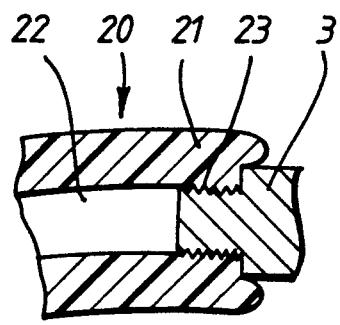

In a modified form of the invention shown in FIG. 5, a segment or connector, e.g. a segment 20, comprises an outer hollow container 21 having an interior space 22 there being at least one opening e.g. opening 23 from the space 22. A biodegradable plug is provided to seal the opening 23 and preferably such plug comprises a male threaded end of a connector 3, as shown. The container 21 is preferably non permeable but may comprise a matrix of a substance and a carrier therefor as above described, and the biodegradable plug could in fact be part or all of the wall of the container 21.

The interior space 23 contains a biologically useful substance e.g. progesterone in a releasable form e.g. it may be in paste or liquid form. Degradation of the plug 23 will then make the substance in the space 22 available in the form of a comparatively large dose of substances when the plug is bio-degradably removed from the opening 23.

In an additional aspect of the invention, the device is provided in a form for insertion into the animal. In this aspect, the coil is extended into its first configuration and is retained within an applicator 10 as shown in FIG. 2. The applicator 10 comprises a chamber 11 defined by walls, and is so dimensioned and configured as to retain the device when the device in the first configuration. The applicator 10 further includes a plunger 12 to eject the device from the chamber 11.

The use of the invention will now be described.

In use, the device according to the invention is inserted into a body cavity of an animal, such as the rumen of a ruminant animal, in order to release a desired substance such as a drug into the body cavity over time.

The coil 1 from the device is assembled by connecting together a plurality of segments 2 by way of connectors 3. It is an advantage that the drug dosage can be regulated by altering the number of drug containing segments and/or. connectors provided for insertion into a selected animal.

The coil 1, extended into the first configuration, is retained within the chamber 11 of an applicator 10 (FIG. 2). The applicator 10 is then pushed down the oesophagus, or other body passage 17, of the animal, and the plunger 12 is operated to eject the device from the applicator into a body cavity 15 such as the rumen. The applicator may then be withdrawn.

When the coil 1 is ejected from the applicator chamber 11, it is resiliently biased into the expanded coil formation shown in FIG. 1 and is thereby retained within the body cavity 15, by expanding against the walls of the body cavity 15 and being of too great a diameter to pass through the entry and exit passages 17.

The drug or other substance is then gradually released from the device 1 over time, for example, by being leached from the impregnated material by the action of body fluids. The connectors 3 and/or the segments 2 are also gradually degraded by body fluids, preferably at a slower rate than the leaching or other release so that after release of the desired substance of the substance is complete, the connectors 3 and/or the segments 2 are sufficiently degraded to release the segments 2 from connection with one another. The segments 2 are then able to pass through one or other of the passages 17 exiting from the body cavity 16 e.g. by excretion and may thus be released from the animal. However in some cases it may be desirable to have segments retained in the rumen to permit release of core drug or other substance as above described with reference to FIG. 5.

The amount of drug or other substance delivered to the animal may be controlled by controlling the amount of substance impregnated or otherwise incorporated into the device, and the size, number and configuration of the segments 2 and/or connectors 3. With the device according to FIG. 5, degrading of the plug permits rapid leaching of the substance in the space 22 giving a heavy dose when the plug is substantially removed.

As an alternative to the progesterone mentioned above as a specific desired substance for administration by a device according to the invention anthelmintics are suggested. The biodegradable parts of the invention may be made from a plastics material sold under the trade name of BIO POL.

An aliphatic polyester (poly [3-Hydroxy butyrate] made by I.C.I. A further material is selected from a range of master batches (colourants) which, when added to a pure resin, impart bio degradability to the resin. The range is made by Constab Polymer Chemic. A particular product is BIO9003HD to be used with polyethylene.

Thus it can be seen that a device is provided by the invention for insertion into a body cavity of an animal to release a desired substance therein over time. The device is able to be readily positioned in the animal, is retained therein without causing a blockage within the animal's system, and may be readily naturally eliminated from the animal once the release is complete.

What is claimed is:

1. A device for insertion into a body cavity of an animal, when in one configuration and to lie against walls of said body cavity in a second expanded configuration, said device comprising a set of interconnected primary elements, and a set of secondary elements forming connectors between said primary elements and connecting said primary elements in the form of a coil, wherein elements of at least one of said sets are constructed of a bio-degradable material.

2. A device as claimed in claim 1 wherein said coil is in the form of a helix.

3. A device as claimed in claim 2 wherein said elements of at least one of said sets are resiliently flexible.

4. A device as claimed in claim 1 wherein at least one of said primary elements comprises a container having walls which form at least one opening to said container and a biodegradable plug in said opening and a desired substance within said container in a releasable form, degradation of said plug releasing said substance from said container.

5. A device as claimed in claim 4 wherein said plug comprises a connector sealing said opening.

6. A device as claimed in claim 5 adapted, configured and dimensioned to pass through the oesophagus of a predetermined ruminant animal when in said one configuration, and to be retained in the rumen of said animal when in said second configuration, wherein at least one of said primary elements comprises a container having walls which form at least one opening to said container and a biodegradable plug in said opening and a desired substance within said container, in a releasable form, degradation of said plug releasing said substance from said container.

7. A device as claimed in claim 4 wherein said container is of a non permeable material.

8. A device as claimed in claim 4 wherein said container has a matrix of a releasable substance and a carrier therefor.

9. A device as claimed in claim 1, adapted configured and dimensioned to pass through oesophagus of a predetermined ruminant animal when in said one configuration and to be retained in the rumen of said animal when in said second configuration for a substantially predetermined period of time after which said elements constructed of biodegradable material are degraded by animal fluids of the animal to cause separation of the device into parts small enough to enable such parts to be excreted naturally by the animal.

10. A device according to claim 1 in combination with an applicator for said device, the applicator comprising a chamber so dimensioned and configured as to retain said device in said one configuration and a plunger portion to eject said device from said chamber.

11. A device for insertion into a body cavity of an animal to release a desired substance therein over time, said device being in the form of a helical coil at least parts of which are resilient, said helical coil at least partly including a desired substance in a form adapted to be released from said device over time, said helical coil being resiliently extendible into a first configuration having dimensions small enough so that said helical coil is able to be passed through body passages of said animal into the desired body cavity, and being resiliently biased towards a second expanded configuration retaining its helical form whereby the coil expands until said coil presses against the inner lining of said body cavity in order to be retained within the body cavity.

12. A device as claimed in claim 11 wherein said coil comprises a plurality of primary elements joined together by at least one secondary element forming a connector between the primary elements, at least one of said elements being constructed of a bio-degradable material, said bio-degradable material being selected so as to be degraded by body fluids within said body cavity over time so as to release said primary elements from connection with one another after substantially all of said substance has been released from said device.

13. A device as claimed in claim 12 wherein said secondary element is screw fastened to said primary elements.

14. A device as claimed in claim 12 wherein said primary elements each comprise a spine and a moulded material impregnated with said substance on the outer surface of said spine.

15. A device as claimed in claim 14 wherein said moulded material comprises a silicone elastomer.

16. A device as claimed in claim 14 wherein said spine is constructed of a polyamide or the like resilient plastics material.

* * * * *